United States Patent
Buchschuster

(10) Patent No.: US 10,689,785 B2
(45) Date of Patent: Jun. 23, 2020

(54) COMPRESSION KNIT FABRIC FROM A BASE KNIT AND AN ELASTIC WEFT YARN INSERTED THEREIN AS WELL AS METHOD FOR PRODUCTION OF A COMPRESSION KNIT FABRIC

(71) Applicant: Julius Zorn GmbH, Aichach (DE)

(72) Inventor: Martin Buchschuster, Meitingen (DE)

(73) Assignee: JULIUS ZORN GMBH, Aichach (DE)

( * ) Notice: Subject to any disclaimer, the term of this patent is extended or adjusted under 35 U.S.C. 154(b) by 47 days.

(21) Appl. No.: 15/992,419

(22) Filed: May 30, 2018

(65) Prior Publication Data
US 2018/0347082 A1 Dec. 6, 2018

(30) Foreign Application Priority Data
May 30, 2017 (DE) .................... 20 2017 103 246 U

(51) Int. Cl.
*D04B 1/18* (2006.01)
*D04B 1/10* (2006.01)
(Continued)

(52) U.S. Cl.
CPC ................ *D04B 1/18* (2013.01); *A61F 13/08* (2013.01); *D04B 1/102* (2013.01); *D04B 1/265* (2013.01); *D10B 2509/028* (2013.01)

(58) Field of Classification Search
CPC .......... D04B 1/123; D04B 1/18; D04B 1/265; D04B 7/14; D04B 7/18; D04B 9/16;
(Continued)

(56) References Cited

U.S. PATENT DOCUMENTS 219,619 A * 9/1879 Chase ...................... D04B 9/16
66/10
627,945 A * 6/1899 Waterfield ............... D04B 1/18
66/190
(Continued)

FOREIGN PATENT DOCUMENTS

DE 1815483 U 7/1960
DE 2047566 A1 4/1971
(Continued)

OTHER PUBLICATIONS

Result of Search Report for German Application No. 20 2017 103 246.9 filed May 30, 2017.
(Continued)

*Primary Examiner* — Danny Worrell
(74) *Attorney, Agent, or Firm* — Paul D. Bianco; Fleit Intellectual Property Law

(57) ABSTRACT

A compression knit fabric consisting of a base knit and an elastic weft yarn inserted therein. The base knit is formed from at least one knitting yarn, and the weft yarn is inserted in weft yarn courses between two consecutive stitch courses of the base knit. The knitting yarn in each stitch course of the base knit is knit in alternation as loop stitch and tuck, so that the knitting yarn forms a tuck stitch between two loops of a stitch course of the base knit. The weft yarn is inserted between adjacent stitch courses of the base knit in alternation as tuck and float so that the weft yarn floats between two tuck stitches of a weft yarn course. The alternating sequence of loop stitch and tuck in consecutive stitch courses of the base knit is offset by a stitch relative to the alternating sequence of tuck and float in consecutive weft yarn courses.

16 Claims, 4 Drawing Sheets

(51) Int. Cl.
*D04B 1/26* (2006.01)
*A61F 13/08* (2006.01)

(58) Field of Classification Search
CPC .. D04B 9/52; D04B 1/102; D04B 1/26; A61F 13/08
USPC .......................................................... 66/190
See application file for complete search history.

(56) References Cited

U.S. PATENT DOCUMENTS

| | | | | |
|---|---|---|---|---|
| 930,180 | A * | 8/1909 | Horn | D04B 1/24 66/171 |
| 1,386,444 | A * | 8/1921 | Stibbe | D04B 1/00 66/190 |
| 1,577,752 | A * | 3/1926 | Price | D04B 1/26 66/172 R |
| 1,976,885 | A * | 10/1934 | Levin | D04B 1/00 66/190 |
| 2,015,608 | A * | 9/1935 | Southwick, Jr. | D04B 1/26 66/189 |
| 2,033,096 | A * | 3/1936 | Drumheller | D04B 1/18 66/190 |
| 2,108,925 | A * | 2/1938 | Raynor | D04B 1/14 66/190 |
| 2,111,472 | A * | 3/1938 | Horn | D04B 1/18 66/189 |
| 2,127,780 | A * | 8/1938 | Marshall | D04B 9/54 66/172 E |
| 2,166,166 | A * | 7/1939 | Larkin | D04B 1/10 66/170 |
| 3,159,990 | A * | 12/1964 | Monday | D04B 9/54 66/172 E |
| 3,287,938 | A | 11/1966 | Knohl | |
| 3,975,929 | A | 8/1976 | Fregeolle | |
| 10,011,926 | B2 * | 7/2018 | Gaither | A61F 13/08 |
| 2002/0108405 | A1 * | 8/2002 | Yakopson | A41B 9/02 66/177 |

FOREIGN PATENT DOCUMENTS

| | | |
|---|---|---|
| DE | 102008059241 A1 | 6/2010 |
| DE | 102015110313 A1 | 12/2016 |
| EP | 1895036 A1 | 3/2008 |
| GB | 1276826 A | 6/1972 |

OTHER PUBLICATIONS

European Search Report dated Oct. 22, 2018 for European Application No. EP 18 16 7028.

* cited by examiner

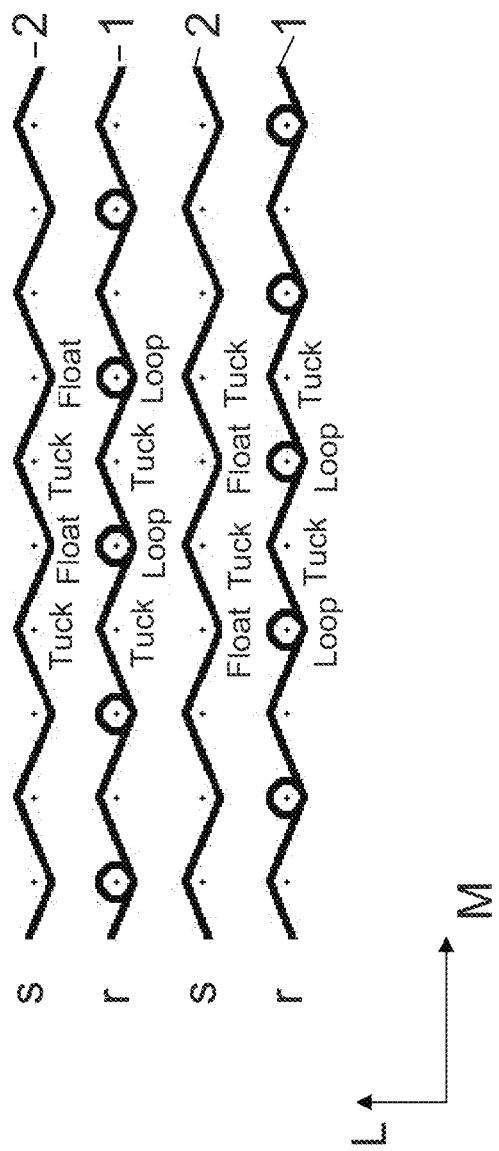

COMPRESSION KNIT FABRIC FROM A BASE KNIT AND AN ELASTIC WEFT YARN INSERTED THEREIN AS WELL AS METHOD FOR PRODUCTION OF A COMPRESSION KNIT FABRIC

FIELD OF THE DISCLOSURE

The disclosure relates to a compression knit fabric and a method for production of a compression knit fabric.

BACKGROUND

Compression knit fabrics are used, for example, to produce compression articles, like compression stockings or compression bandages. Such compression knit fabrics can be produced especially as circular knits on a circular knitting machine or recently also on flat knitting machines. The base knit in the compression knit fabrics known from the prior art is formed from at least one elastic or inelastic knitting yarn, and a compression-producing elastic weft yarn is inserted into the base knit in each second knit row. The elastic weft yarns can be an elastane or rubber yarn or a winding yarn with an elastic core yarn around which a yarn is wound.

Owing to the elasticity of the weft yarn, the tubular compression knit fabric formed as a circular knit acquires its compressive properties in the peripheral direction. When the tubular compression knit is positioned, for example, as a compression stocking on a leg of a patient, the compression knit generates a compression on the yarn through the elasticity of the elastic weft yarn. Other compression articles, like compression sleeves, are also known from the prior art for treatment of vein diseases and lymphatic insufficiencies.

If an elastane or rubber yarn is used as elastic weft yarn and, as is common in the known compression knits, is inserted as tuck and float between two consecutive stitching rows of the base knit, the elastic weft yarn comes to lie at the sites at which it appears to float on the surface of the compression knit. When the compression knit is positioned on a body part, the elastic weft yarn thus comes into contact with the skin of the patient. This can lead to skin irritation when there are incompatibilities of the patient relative to the material of the weft yarn. When a winding yarn is used as elastic weft yarn, in comparison with the knitting yarns of the base knit, this has a much greater thickness and the yarn that is wound around the elastic core yarn in the winding yarn exhibits high friction. Because of the thickness of the elastic weft yarn from a winding yarn and the high friction of the surface of the winding yarn, difficulties occur when a compression article produced from the compression knit fabric is put on, because strong friction of the surface of the elastic weft yarn against the skin of the patient occurs.

To solve this problem, a compression circular knit is proposed in DE 10 2015 110 313 A1, which consists of at least two different knit areas, in which a first knit area is laid out as a compressive knit area in the form of an ordinary compression knit from an elastic base knit yarn and a weft yarn inserted in it as tuck and float, and a second knit area is provided in which the elastic base knit yarn and the elastic compression-producing yarn are knit together, forming a loop. On the one hand, a supporting and compressive effect can be achieved with the second knit area, the attainable compression being determined by the elastic yarn joined with the base knit yarn to form a loop and is less high in the peripheral direction than in the ordinary compression knit of the first knit area. However, the compression-producing elastic yarn in the second knit area lies at least largely in the knitted fabric interior, since the compression-producing elastic yarn is joined via stitches in the base knit. As a result, a reduced contact of the compression-producing elastic yarn with the skin of a patient is guaranteed at least in the two knit areas, so that skin irritation is reduced, on the one hand, and putting on of the compression article is facilitated, on the other.

However, the compression circular knit proposed in DE 10 2015 110 313 A1 only leads to a reduction in contact between the compression-producing elastic yarn and the skin of a patient in areas and therefore is also only partially facilitative when a compression article produced from the compression knit fabric is put on.

SUMMARY

One aspect of the disclosure is to modify a generic compression knit fabric so that essential facilitation is achieved when a compression article produced from the compression knit fabric is put on and the risk of skin irritation can be largely avoided. Another aspect is to provide a method for production of such a compression knit fabric that can be conducted in automatic fashion, especially on circular knitting machines or also on flat knitting machines.

These aspects are disclosed with the compression knit fabric and method for production of a compression knit fabric as described herein. Preferred embodiments of the compression knit fabric and the method are also disclosed.

The compression knit fabric according to the disclosure consists of a base knit of at least one knitting yarn and an elastic weft yarn inserted into the base knit, wherein the elastic weft yarn is inserted in each weft yarn row between two consecutive stitch rows of the base knit. The knitting yarn in each stitch row of the base knit is knitted alternately as stitch and tuck so that the knitting yarn forms a tuck stitch between two stitches of a stitch row of the base knit. The weft yarn is inserted between adjacent stitch rows of the base knit in alternation as a tuck and float, so that the weft yarn floats between two tuck stitches of a weft yarn row. The alternating sequence of stitch and tuck in consecutive stitch rows of the base knit is then arranged offset by one stitch, and the alternating sequence of tuck and float in consecutive weft yarn rows is also arranged offset by one stitch.

This design of the base knit and insertion of the elastic weft yarn between two consecutive stitch rows of the base knit means that the tuck stitch of the elastic weft yarn is cast into the following stitch (i.e., in a stitch of the following stitch row of the base knit) and therefore floats at this site. Overall, the elastic weft yarn therefore lies freely in each weft yarn row without binding points in the base knit. In addition, the weft yarn lies fully in the compression knit fabric, i.e., over its entire length in the peripheral direction of a tubular compression circular knit on the inside, i.e., within the base knit and therefore does not appear on the surface of the compression knit fabric. On the one hand, contact between the surface of the elastic weft yarn and the skin of a patient is (almost) thereby completely avoided, for which reason virtually no skin irritation can occur. Moreover, because of complete embedding of the elastic weft yarn in the base knit, the putting on of a compression article produced from the compression knit fabric is facilitated, because the rough surface of the weft yarn formed as winding yarn, for example, can scarcely come into contact with the skin of a patient. The friction that arises during putting on of a compression article between the inside of the knit of the compression article and the skin of a patient is essentially influenced in the compression knit according to the disclosure by the friction properties of the surface of the knitting yarn. Since the knitting yarn, in comparison with elastic weft yarn, is generally much thinner and has a much smoother surface in comparison with a weft yarn formed as a winding yarn, the friction produced in the knit according to the disclosure by the knitting yarn on the skin of a patient is much less than the friction produced in ordinary compression knits by the thick weft yarn lying freely on the inside of the knit. A compression article produced from the compression knit fabric according to the disclosure therefore permits much easier putting on owing to the limited friction between the inside of the knit and the skin of a patient.

The knitting yarn from which the base knit can be knit in the form of a right-left knit fabric, for example, is expediently a yarn with limited elasticity. The stretchability of the knitting yarn is expediently less than the stretchability of the elastic weft yarn. It is also possible to use a non-elastic knitting yarn.

For application of the compression knit according to the disclosure as a compression article for treatment of vein diseases or lymphatic insufficiencies, a winding yarn with an elastic core yarn is preferably used as knitting yarn. In addition to the knitting yarn and the elastic weft yarn inserted into the base knit, additional yarns can optionally be incorporated in the base knit, for example, a stitch-forming knitted rubber-elastic yarn that also makes the compression knit fabric stretchable in the longitudinal direction.

The elastic weft yarn is preferably a winding yarn with a highly elastic core yarn and a wound yarn. As an alternative, an (unwound) elastane or rubber yarn can also be used as elastic weft yarn. The weft yarn preferably has a thickness in the range from 200 dtex to 1500 dtex. The thickness of the knitting yarn, on the other hand, is generally much smaller, for example, by a factor of 2 to 20, but preferably lies at at least 44 dtex.

The base knit can be designed, for example, as a single jersey knit. Other stitch patterns, however, are conceivable.

The compression knit fabric according to the disclosure is expediently formed as a circular knit, i.e., in the form of a tube, so that seamless compression articles, like compression stockings or sleeves, can be produced from the compression knit.

The compression knit fabric according to the disclosure can be produced with the method according to the disclosure as a circular knit on a circular knitting machine or a flat knitting machine or also as a flat knit on a flat knitting machine.

BRIEF DESCRIPTION OF THE DRAWINGS

These and other advantages as well as features of the compression knit according to the disclosure are apparent from the following embodiment example further described with reference to the accompanying drawings. The drawings show:

FIG. 2: Schematic depiction of the grain of the embodiment of a compression knit fabric according to the disclosure according to FIG. 1A;

Figure 3:
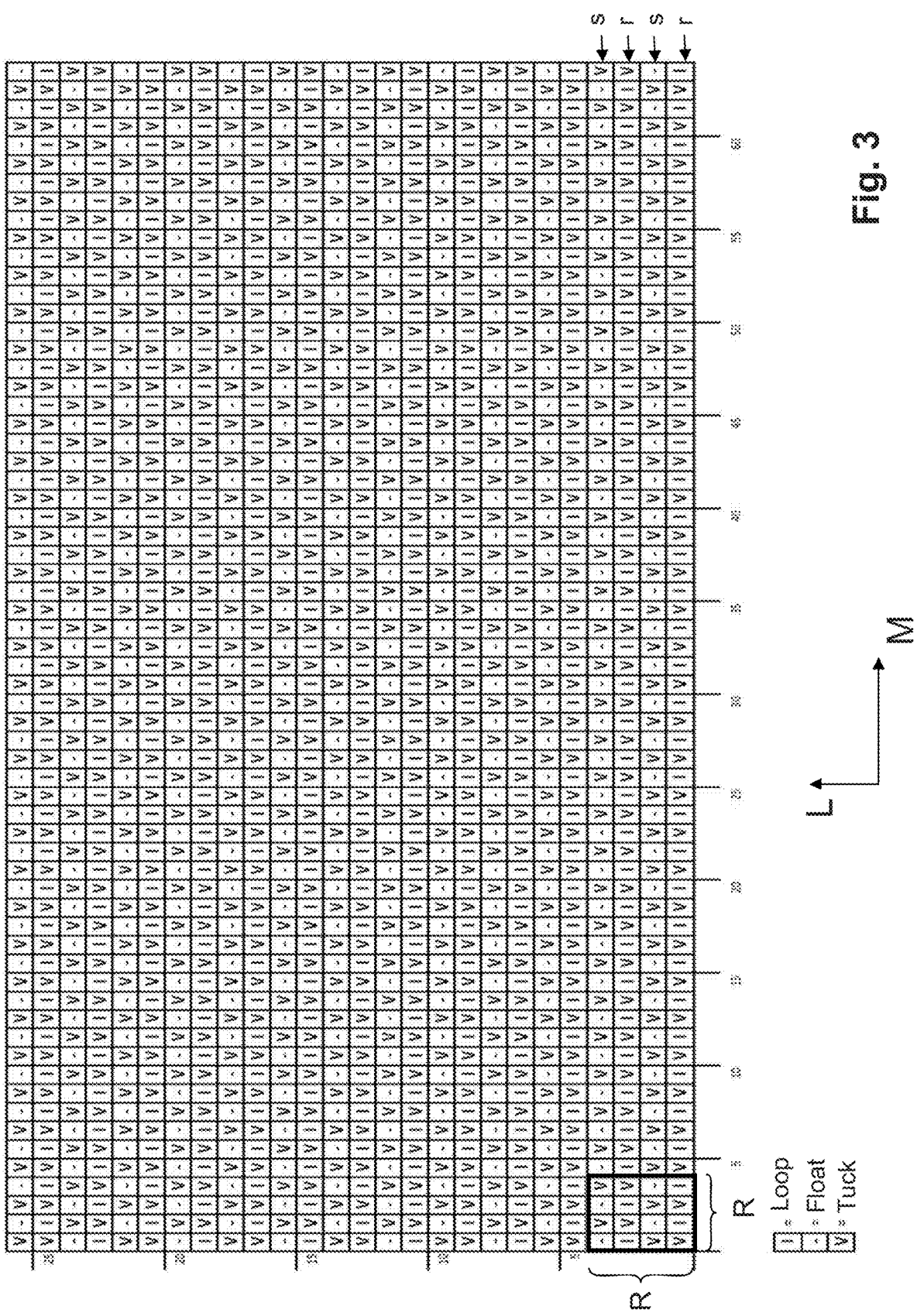
FIG. 3: Technical patterns of the compression knit of FIG. 1A.

The following symbols with the following meaning are used in the drawing of the grain of FIG. 2 and the technical pattern of FIG. 3:
I=stitch (loop)
-=float (miss)
V=tuck

DETAILED DESCRIPTION

The base knit in the embodiment example of a compression knit fabric according to the disclosure depicted only as an example to explain the disclosure in FIGS. 1-3 is formed from a (single) knitting yarn 1, in which the base knit is designed as a single jersey knit. The knitting yarn 1 is then knitted in each stitch row r of the base knit in alternation as loop stitch (I) and tuck (V) so that the knitting yarn 1 forms a tuck stitch between two loops (I) of a stitch row r of the base knit.

A weft yarn row s is arranged between adjacent stitch rows r of the base knit, in which a weft yarn 2 is inserted. The weft yarn 2 is then inserted in each weft yarn row s in alternation as tuck (V) and float (-) so that the weft yarn 2 floats between two tuck stitches (V) of a weft yarn row s.

The alternating sequence of loop (I) and tuck (V) of stitch rows r following in longitudinal direction L of the base knit is then arranged offset by one stitch, as is apparent from the figures, i.e., the stitches (I) in the longitudinal direction L of the consecutive stitch courses r of the base knit are arranged offset by one loop stitch in the stitch wale and accordingly the tuck stitches (V) lying between two loop stitches (I) are offset by one stitch in the stitch wale M. The alternating sequence of tuck (V) and float (-) of the weft yarn 2 is also offset accordingly by one stitch in consecutive weft yarn courses s.

Because of the arrangement of the sequence of stitch (I) and tuck (V) offset by a stitch in consecutive stitch courses r of the base knit and the alternative sequence of tuck (V) and float (-), that is also offset by one stitch in consecutive weft yarn courses s, the elastic weft yarn is initially inserted in each weft yarn course s in alternation as tuck (V) and as float (-). The following stitch (I) (in the following stitch course r of the base knit), however, throws off the elastic weft yarn 2, and therefore a float (-) of the weft yarn (2) arises at this site.

Figure 1A:
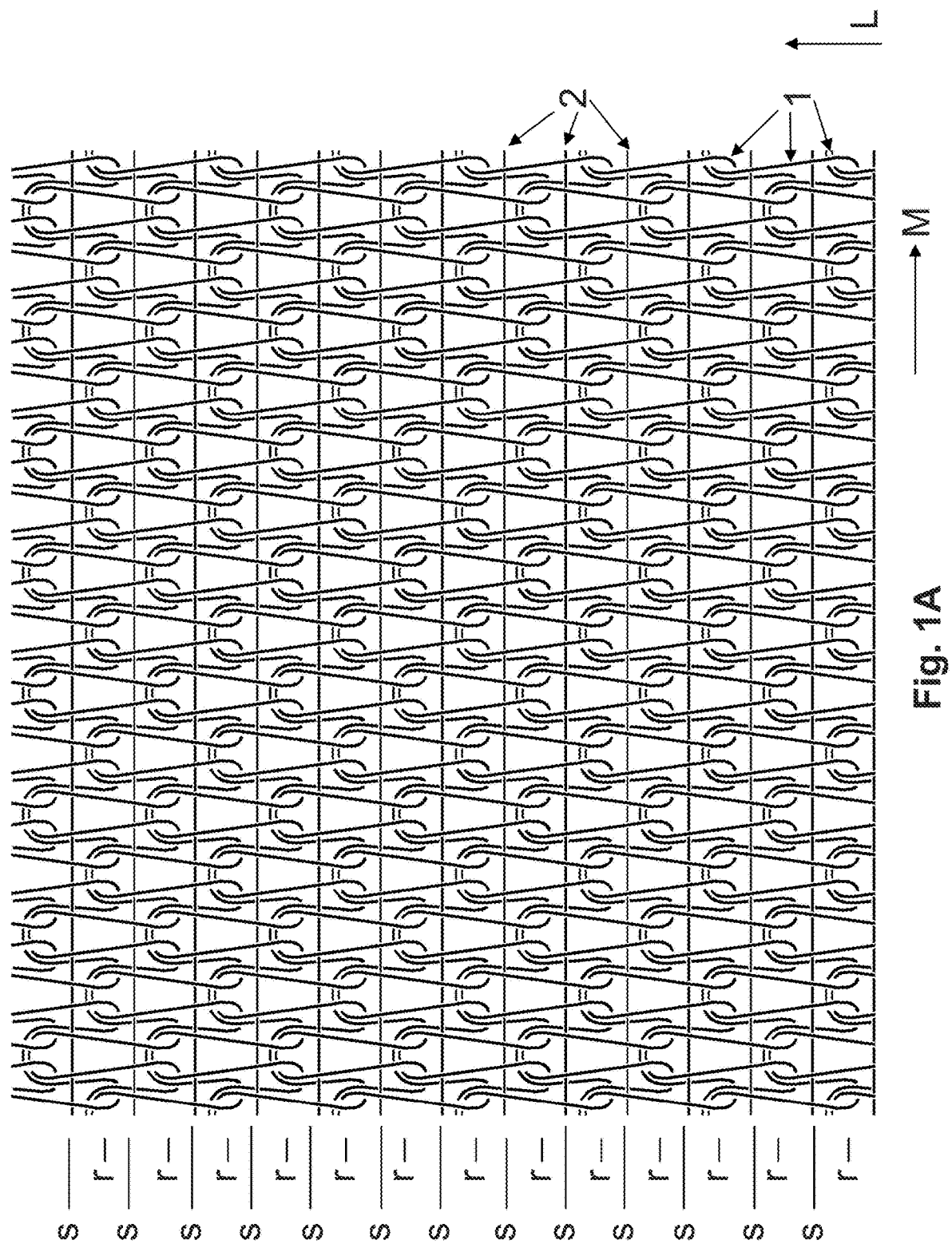
FIG. 1A: A stitch pattern of one embodiment of the compression knit fabric according to the disclosure (right product side)
Figure 1B:
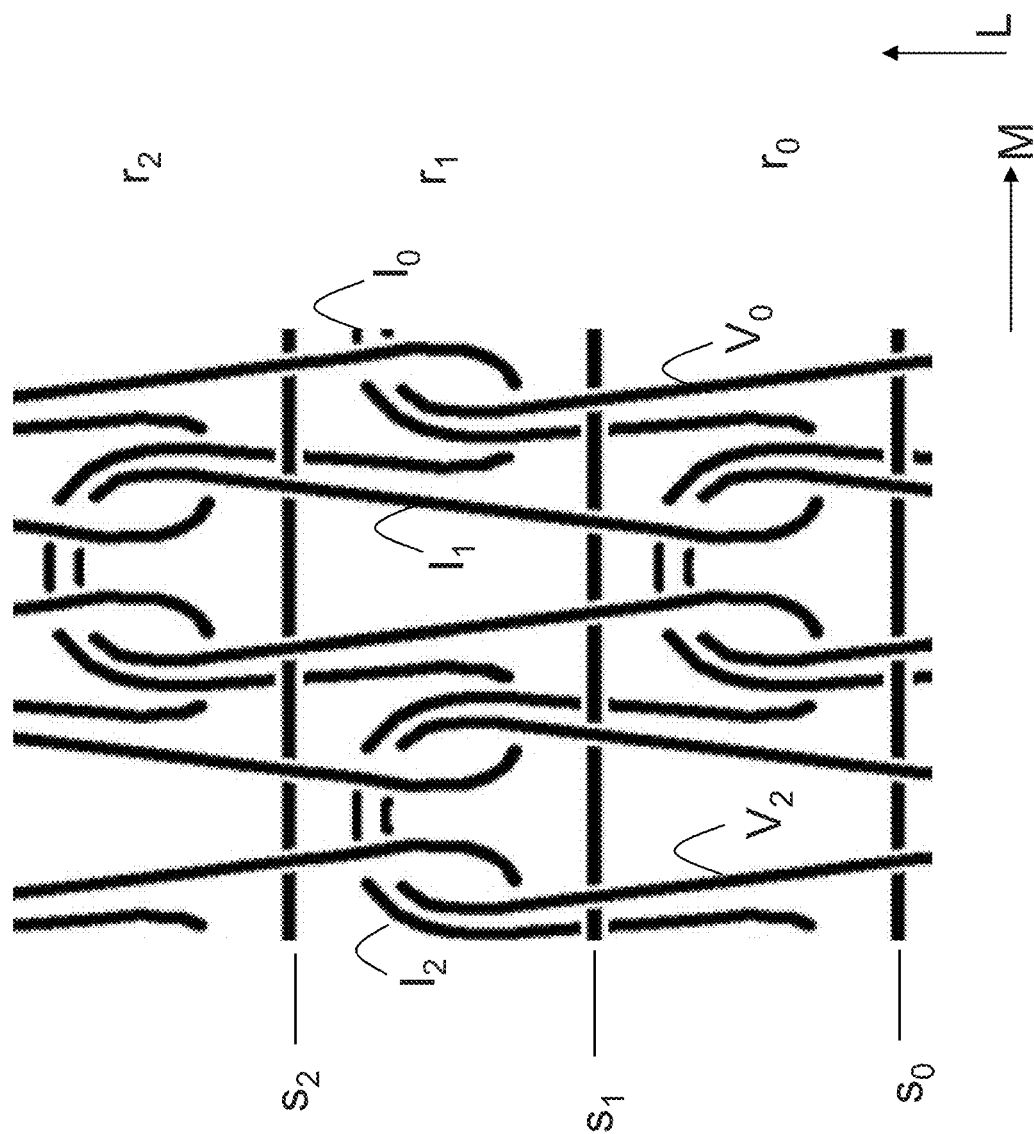
FIG. 1B: An enlarged cutout of the stitch pattern of FIG. 1A (right product side)

As is apparent from the detail view of FIG. 1B, which shows an enlarged cutout of the stitch pattern of FIG. 1A on the right product side, the weft yarn 2 in a certain weft yarn course $s_1$ lies behind a first stitch $I_1$ from the adjacent stitch course $r_1$ of the base knit and in front of the second stitch 12 adjacent to this first stitch $I_1$ in the stitch wale M. At the same time the weft yarn 2 lies behind the tuck stitch $V_2$ raised from the underlying stitch course $r_0$ so that the weft yarn 2 in the specific weft yarn course $s_1$ passes between the adjacent second stitch $I_2$ and the raised tuck stitch $V_2$.

As is apparent from FIG. 3, the knit has a periodically recurring repeat R both in the stitch wale M and in the longitudinal direction L of the knit. The repeat R can then extend especially in the stitch wale M over four stitches and in the longitudinal direction L over four consecutive courses (i.e., over two stitch courses r of the base knit and two weft yarn courses s).

As is apparent from the stitch pattern of FIG. 1A, the weft yarn lies freely over its entire length (which extends in the stitch wale M) without binding points in the base knit. The elastic weft yarn 2 is therefore freely movable in the base knit. The elastic weft yarn 2 because of its elasticity produces stretchability of the knit in the stitch wale M so that, in a compression knit made as a circular knit, a compression effect is produced in the peripheral direction of the tubular circular knit.

The weft yarn 1, which can also be an elastic yarn, when an elastic weft yarn is used, also contributes to a limited extent to stretchability and therefore to creation of a compression effect of the compression knit fabric, but to a much lesser degree than the elastic weft yarn 2 freely inserted in the base knit.

Owing to the fact that weft yarn is inserted freely in the base knit fabric without binding points, the elasticity of the elastic weft yarn 2 is not hindered during stretching of the compression knit fabric in the stitch wale M. Thus, a precisely defined stretchability that depends exclusively on the elasticity of the weft yarn 2 is implemented. In production of compression articles from the compression knit according to the disclosure, precisely defined compression pressures can therefore be generated. Especially in compression stockings, which have a compression pressure trend that diminishes from the distal to proximal end, precise adjustment of a medically desired pressure gradient is thereby possible.

It is apparent from the stitch pattern of FIG. 1A that the weft yarn 2 lies within the base knit over its entire length that extends in stitch wale M. Elastic weft yarn 2 is therefore fully in the interior, differently than in the known compression knit fabrics. This improves the putting on of a compression article produced from the compression knit fabric according to the disclosure owing to the reduced friction between the interior of the knit of the compression article and the skin of a patient.

The compression knit fabric according to the disclosure can also be used only in areas in compression articles and in this case combined with other knit fabric structures. For example, a section formed according to the disclosure can be seamlessly stitched with a knit section from an ordinary compression knit or with knit sections without inserted weft yarn.

What is claimed is:

1. A compression knit fabric consisting of a base knit and an elastic weft yarn inserted therein, wherein the base knit is formed from at least one knitting yarn and the weft yarn is inserted in weft yarn courses between two consecutive stitch courses of the base knit, wherein
    the knitting yarn in each stitch course of the base knit is stitched alternately as loop stitch and tuck, so that the knitting yarn forms a tuck stitch between two loops of a stitch course of the base knit,
    the weft yarn is inserted between adjacent stitch courses of the base knit alternatively as tuck and float, so that the weft yarn floats between two tuck stitches of a weft yarn course,
    a weft yarn course is arranged between two stitched courses of the base knit following each other in the longitudinal direction of the knit,
    the alternating sequence of loop and tuck in consecutive stitch courses of the base knit is offset by one stitch, and
    the alternating sequence of tuck and float in consecutive weft yarn courses is offset by one stitch.

2. The compression knit fabric according to claim 1, wherein the weft yarn is elastic.

3. The compression knit fabric according to claim 2, wherein the elastic weft yarn is a winding yarn with elastic core yarns, wherein the knitting yarn has a smaller thickness than the weft yarn.

4. The compression knit fabric according to claim 1, wherein the elastic weft yarn is a winding yarn with a highly elastic core yarn or an elastane or rubber yarn, wherein the weft yarn has a thickness in the range from 200 to 1500 dtex.

5. The compression knit fabric according to claim 1, wherein the weft yarn in each weft yarn course is initially inserted in alternation as tuck and float and the subsequent loop of the adjacent stitch course of the base knit throws out the weft yarn, so that a float of the weft yarn is formed.

6. The compression knit fabric according to claim 1, wherein the weft yarn is inserted in the base knit without binding points.

7. The compression knit fabric according to claim 1, wherein weft yarn lies fully on the inside in the compression knit and does not appear on the surface.

8. The compression knit fabric according to claim 1, wherein the base knit is a single jersey knit and/or the base knit is knit in a 1:1 stitch.

9. The compression knit fabric according to claim 1, wherein the compression knit fabric is a circular knit.

10. The compression knit fabric according to claim 1, wherein the compression knit fabric has a periodically recurring repeat both in the stitch wale and in the longitudinal direction of the knit.

11. The compression knit fabric according to claim 1, wherein the weft yarn in a certain weft yarn course lies behind a first loop stitch from the adjacent stitch course of the base knit and in front of the second loop stitch adjacent to this stitch in the stitch wale and at the same time lies behind the tuck stitch raised from the underlying stitch course, so that the weft yarn in the specific weft yarn course passes between the adjacent second loop stitch and the tuck stitch.

12. A compression article produced from a compression knit fabric according to claim 1.

13. The compression article of claim 12, wherein the compression article is a compression stocking or sleeve.

14. A method for production of a compression knit fabric from a base knit and an elastic weft yarn inserted therein, wherein the base knit is knit from at least one knitting yarn and the weft yarn is inserted in weft yarn course between two consecutive stitch courses of the base knit, wherein
    the knitting yarn in each stitch course of the base knit is knit in alternation as loop stitch and tuck, so that the knitting yarn forms a tuck stitch between two loops of a stitch course of the base knit,
    the weft yarn is inserted alternatively between adjacent stitch courses of the base knit as tuck and float, so that the weft yarn floats between two tuck stitches of a weft yarn course,
    a weft yarn course is arranged between two stitched courses of the base knit following each other in the longitudinal direction of the knit,
    the alternating sequence of loop stitch and tuck in consecutive stitch courses of the base knit is offset by one stitch, and
    the alternating sequence of tuck and float in consecutive weft yarn courses is offset by one stitch.

15. The method according to claim 14, wherein the tuck stitch of the elastic weft yarn by insertion of the elastic weft yarn between two consecutive stitch courses of the base stitch is thrown into a loop stitch of the subsequent stitch course of the base knit and therefore floats at this location.

16. A compression knit fabric consisting of a base knit and an elastic weft yarn inserted therein, wherein the base knit is formed from at least one knitting yarn and the weft yarn is inserted in weft yarn courses between two consecutive stitch courses of the base knit, wherein the knitting yarn in each stitch course of the base knit is stitched alternately as loop stitch and tuck, so that the knitting yarn forms a tuck stitch between two loops of a stitch course of the base knit,
the weft yarn is inserted between adjacent stitch courses of the base knit alternatively as tuck and float, so that the weft yarn floats between two tuck stitches of a weft yarn course,
the alternating sequence of loop and tuck in consecutive stitch courses of the base knit is offset by one stitch, and
the alternating sequence of tuck and float in consecutive weft yarn courses is offset by one stitch, and
the weft yarn lies fully on the inside in the compression knit and does not appear on the surface.

\* \* \* \* \*